(12) United States Patent
Hofmann et al.

(10) Patent No.: US 6,192,270 B1
(45) Date of Patent: Feb. 20, 2001

(54) APPARATUS AND METHOD FOR THE DELIVERY OF DRUGS AND GENES INTO TISSUE

(75) Inventors: Gunter A. Hofmann, San Diego; Dietmar Rabussay, Solana Beach; Arnt Tonnessen, San Diego, all of CA (US)

(73) Assignee: Genetronics, Inc., San Diego, CA (US)

(*) Notice: Under 35 U.S.C. 154(b), the term of this patent shall be extended for 0 days.

(21) Appl. No.: 09/134,245

(22) Filed: Aug. 14, 1998

(51) Int. Cl.⁷ .................................. A61N 1/30; A61N 1/00
(52) U.S. Cl. ............................................. 604/20; 607/152
(58) Field of Search .................... 604/20–21; 607/1–3, 607/72, 149, 152

(56) References Cited

U.S. PATENT DOCUMENTS

| | | | |
|---|---|---|---|
| 4,950,229 | * 8/1990 | Sage, Jr. | 604/120 |
| 5,053,001 | * 10/1991 | Reller et al. | 604/20 |
| 5,318,514 | 6/1994 | Hofmann | 604/20 |
| 5,380,272 | * 1/1995 | Gross | 604/20 |
| 5,582,586 | * 12/1996 | Tachibana et al. | 604/20 |
| 5,618,265 | 4/1997 | Myers | 604/20 |
| 5,667,487 | * 9/1997 | Henley | 604/20 |
| 5,704,908 | 1/1998 | Hofmann | 604/21 |
| 5,711,761 | * 1/1998 | Untereker et al. | 604/20 |
| 5,944,685 | * 8/1999 | Muroki | 604/20 |
| 6,009,345 | * 12/1999 | Hofmann | 604/20 |

FOREIGN PATENT DOCUMENTS

| | | | |
|---|---|---|---|
| 0 337 642 | 10/1989 | (EP) . | |
| 0 547 482A1 | * 6/1993 | (EP) | 604/21 |
| WO 95 26781 | 10/1995 | (WO) . | |
| WO 96 00111 | 1/1996 | (WO) . | |
| WO 97 04832 | 2/1997 | (WO) . | |

* cited by examiner

*Primary Examiner*—Sharon Kennedy
(74) *Attorney, Agent, or Firm*—Baker & Maxham

(57) ABSTRACT

An electrode assembly for an apparatus for and a method of trans-surface molecular delivery, including a non-conductive carrier having a proximal surface, a distal surface, and a plurality of through holes from the proximal surface to the distal surface, a first electrode disposed on at least a portion of the distal surface and extending through at least a portion of the plurality of through holes and onto at least a portion of the proximal surface, a second electrode disposed on at least a portion of the proximal surface and in closely spaced relation with the first electrode for engaging a tissue surface through which to apply an electric field, and an insulating barrier that is disposed on at least a portion of the proximal surface of the carrier between the first electrode and the second electrode.

20 Claims, 3 Drawing Sheets

APPARATUS AND METHOD FOR THE DELIVERY OF DRUGS AND GENES INTO TISSUE

BACKGROUND OF THE INVENTION

The present invention relates generally to drug and gene delivery and pertains more particularly to an electrode assembly for an apparatus for a method of trans-surface delivery of genes, drugs, and other molecules through tissue surfaces.

The medical community has long sought improved methods of trans-surface delivery of drugs, genes such as DNA, portions of DNA, chemical agents, or other molecules without physical penetration or invasion of the tissue surface. Several methods involve the electroporation of the tissue surface through the application of an electrical field by means of electrodes on the tissue surface. The field is applied at a predetermined strength and duration in order to make the walls of the tissue surface transiently permeable to permit the molecules to pass through the tissue surface into the underlying tissue. Further electroporation can enable the molecules to enter preselected cells without damaging them. The voltage that must be applied is proportional to the distance between the electrodes. When the space between the electrodes is too great, the generated electric field penetrates deep into the tissue where it causes unpleasant nerve and muscle reaction. The molecules are placed in close proximity to the cells, either in the interstitial tissue surrounding the cells or in a fluid medium containing the cells.

Electroporation can be carried out by a sophisticated electroporation system having programmable power sequence and duration programmed in. For example, a suitable system is disclosed in co-pending application Ser. No. 08/709,615 filed Sep. 9, 1996, entitled ELECTROPORATION EMPLOYING USER-CONFIGURED PULSING SCHEME, now U.S. Pat. No. 5,869,326, granted which is incorporated herein by reference as though fully set forth.

Broadly, the above referenced invention concerns an electroporation apparatus for and method of generating and applying an electric field according to a user-specified pulsing scheme. One example of such a pulsing scheme includes a low voltage pulse of a first duration, immediately followed by a high voltage pulse of a second duration, and immediately followed by a low voltage pulse of a third duration. The low voltage field acts to accumulate molecules at the tissue surface, the appropriately high voltage field acts to create an opening in the tissue surface, and the final low voltage field acts to move the molecules through the tissue surface.

While electroporation provides new pathways through the tissue surface for passages of molecules, it does not provide a needed driving force to those molecules to move them through the tissue surface. As a result, it is desirable to combine electroporation with techniques for providing a driving force such as pressure, ultrasound, electroincorporation, and iontophoresis. First, pressure can be applied mechanically by pressing on the electrode assembly with any suitable means for applying a reasonably uniform pressure over the desired area. Second, ultrasound can be applied by an ultrasound source. Third, electroincorporation can be applied to transport molecules through the tissue surface into the tissue. Fourth, iontophoresis can be applied as the driving force.

Iontophoresis alone, wherein low voltage is applied between widely spaced electrodes for a long period of time, can transport charged molecules through existing pathways such as hair follicles and sweat glands. However, the volumes of molecules transported for a unit of time is very small, and insufficient for many applications. Combining electroporation and iontophoresis can increase the amount transported initially while the created pathways are open. The paths created by the electroporation stay open for a short period of time and then close.

One example of a surface for the trans-surface delivery of molecules is the skin or the stratum corneum (SC). The SC consists of a thin layer of dead cells with a high electrical resistance which presents a major obstacle to the administration of drugs and genes transdermally. However, this layer can be perforated by the administration of short high voltage pulses, which create a dielectric breakdown of the SC forming pores which can allow the passage of molecules.

The tissue surfaces to which the medical profession would like to apply electroporation vary by their size, shape, location, porosity, and accessability, among others. It is desirable that an electrode assembly for an apparatus for and a method of trans-surface molecular delivery be available to accommodate a wide variety of these tissue surfaces.

SUMMARY AND OBJECTS OF THE INVENTION

It is the primary object of the present invention to provide an improved electrode assembly for an apparatus for and a method of trans-surface molecular delivery that can accommodate a wide variety of tissue surfaces.

In accordance with the primary aspect of the present invention, molecules are brought into physical contact with the tissue surface, an electrode is contacted with the tissue surface, and an electric field is applied to the tissue surface by means of the electrode. This forms pores in the tissue surface. Then a driving force is applied to the tissue surface forcing the molecules through the tissue surface into the underlying tissue.

BRIEF DESCRIPTION OF THE DRAWINGS

The above and other objects and advantages of the present invention will be appreciated from the following specification when read in conjunction with the accompanying drawings wherein.

DETAILED DESCRIPTION OF THE PREFERRED EMBODIMENTS

The present invention was devised to provide an electrode assembly for an apparatus for and a method of trans-surface molecular delivery that can accommodate a wide variety of tissue surfaces which vary by their size, shape, location, porosity, and accessability, among others.

A combination of electroporation and iontophoresis can be carried out by a sophisticated combination system having two electrode assemblies and two power supplies. For example, a suitable system is disclosed in co-pending application Ser. No. 08/964,436 filed Nov. 4, 1997, entitled METHOD AND APPARATUS FOR A COMBINATION OF ELECTROPORATION AND IONTOPHORESIS FOR THE DELIVERY OF DRUGS AND GENES, now U.S. Pat. No. 6,009,345, which is incorporated herein by reference as though fully set forth. Broadly, one example of the apparatus disclosed in the above referenced invention is shown here in FIG. 1.

Figure 1:
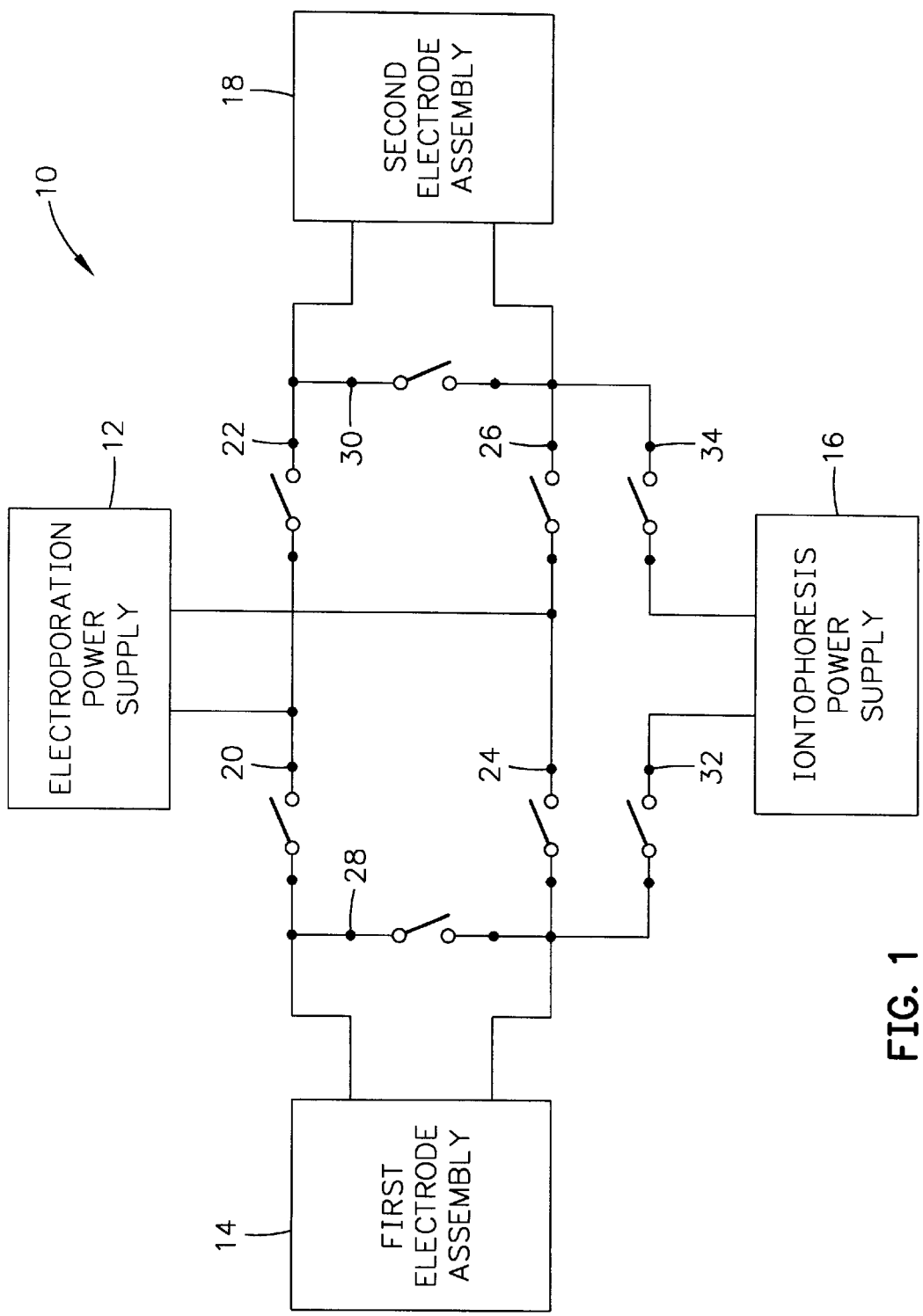
FIG. 1 is a schematic diagram showing a combined electroporation and iontophoresis apparatus.

Turning first to FIG. 1, a schematic diagram of a combined electroporation and iontophoresis apparatus 10 is shown. The apparatus 10 includes an electroporation power supply 12, a first electrode assembly 14, an iontophoresis power supply 16, and a second electrode assembly 18 all of which are connected together by a network of switches (20, 22, 24, 26, 28, 30, 32, and 34) and conductors as shown. The first and second electrode assemblies 14, 18 each include a first and a second electrode (not shown) which are in closely spaced relation to each other.

In operation, electroporation and iontophoresis of the tissue surface are performed sequentially. During electroporation, the electroporation power supply 12 is connected to the first electrode assembly 14 and the second electrode assembly 18 by closing switches 20, 22, 24, and 26 while switches 28, 30, 32, and 34 are held open. During iontophoresis, the iontophoresis power supply 16 is connected to the first electrode assembly 14 and the second electrode assembly 18 by closing switches 28, 30, 32, and 34 while switches 20, 22, 24, and 26 are held open.

Alternatively, the second electrode assembly 18 could include only one electrode (not shown). In such an apparatus 10, switches 22 and 26 would remain permanently open and switch 30 would remain permanently closed. During electroporation, the electroporation power supply 12 is connected to the first electrode assembly 14 by closing switches 20 and 24 while switches 28, 32, and 34 are held open. During iontophoresis, the iontophoresis power supply 16 is connected to the first electrode assembly 14 and the second electrode assembly 18 by closing switches 28, 32, and 34 while switches 20 and 24 are held open.

In one embodiment of the apparatus 10, the first and second electrode assemblies 14, 18 are each a special patch that is applied to spaced areas of the tissue surface. A solution can be contained in the patch which also includes the electrode structure to create the electric field. The electrode structure can be inside or on a surface of the patch. The electrode structure is connected to two conductors outside of the patch so that the electroporation and iontophoresis power supplies 12, 16 can be connected momentarily to these outside conductors to provide a voltage pulse. The patch is preferably provided with an adhesive border to adhere it to the tissue surface. It is also preferably provided with a protective cover which can be peeled off before adhering the patch to the tissue surface.

When iontophoresis is used as the driving force, an electrophoresis electrode is preferably separate from the electroporation electrodes and may also be part of the patch and positioned above the electroporation electrodes. The iontophoresis return electrode may also be remote from the patch electrode assembly or may surround it. An electroporation pulse is first applied to the appropriate electrodes to open pores in the tissue surface. An iontophoresis current is then applied between the appropriate electrodes to draw the drugs or genes through the pores.

Figure 2:
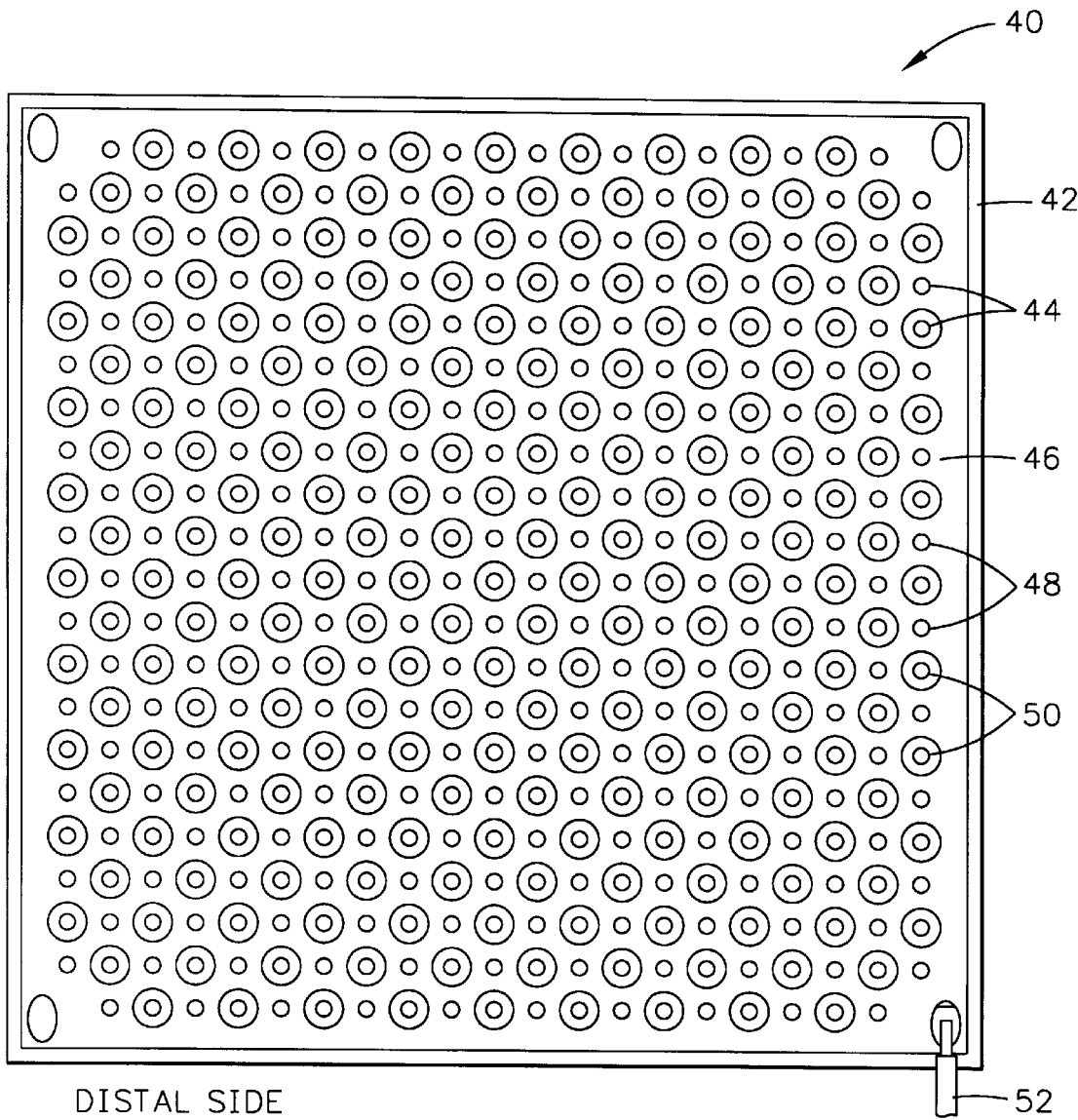
FIG. 2 is a view of a distal side of an electrode assembly according to the present invention.

Turning now to FIG. 2, a view of a distal side of an electrode assembly 40 according to a preferred embodiment of the present invention is shown. The electrode assembly 40 could be substituted for either or both of the first and second electrode assemblies 14, 18 shown in FIG. 1. The electrode assembly 40 includes a non-conductive carrier 42 which has a plurality of through holes 44 which run from the distal side to a proximal side (see FIG. 3). Disposed on the distal side is a first electrode 46. The first electrode 46 extends through a first portion 48 of the plurality of through holes 44 and onto the proximal side. The first electrode 46 is absent around a second portion 50 of the plurality of through holes 44. A first conductor 52 is coupled to the first electrode 46.

Figure 3:
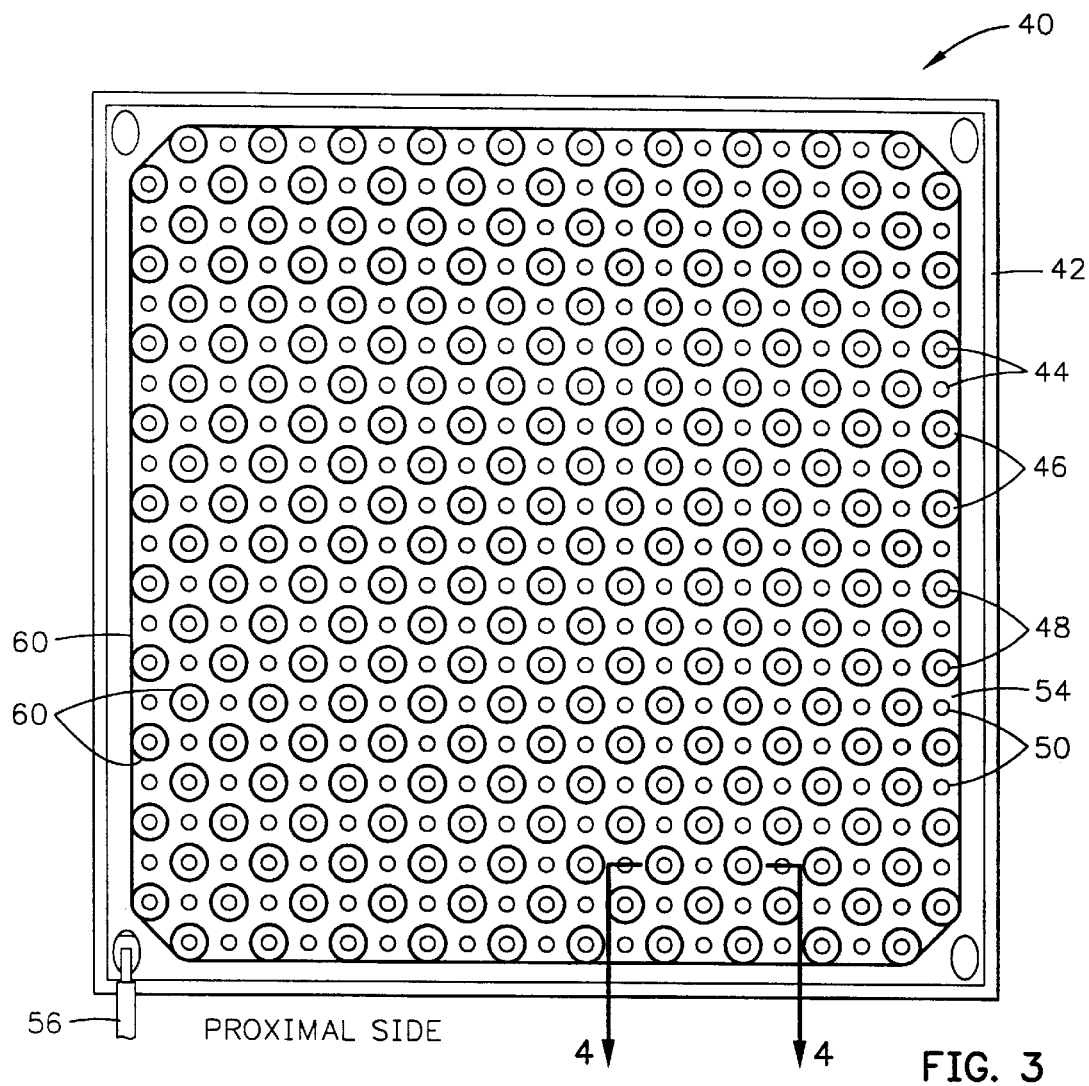
FIG. 3 is a view of a proximal side of an electrode assembly according to the present invention.

Turning now to FIG. 3, a view of a proximal side of an electrode assembly 40 according to a preferred embodiment of the present invention is shown. The proximal side is the side of the electrode assembly 40 that would normally be placed near or against the tissue surface (not shown) that is to be the subject of electroporation. Corresponding to the distal side (see FIG. 2), the proximal side has the plurality of through holes 44. The first electrode 46 extends through the first portion 48 of the plurality of through holes 44 from the distal side. Disposed on the proximal side is a second electrode 54. The second electrode 54 is disposed up to but does not extend through the second portion 50 of the plurality of through holes 44. A second conductor 56 is coupled to the second electrode 54 on the proximal side. Disposed on the proximal side between the first electrode 46 and the second electrode 54 in an insulating barrier 60. The insulating barrier 60 electrically isolates the first electrode 46 from the second electrode 54. In the illustrated embodiment, the insulating barrier 60 has a ring or circular configuration. The first electrode 46 on the proximal side is exposed or presents a plurality of circular or disc shaped contact areas. The second electrode 54 covers the outer area of the electrode assembly 40 between the circular areas of first electrode 46.

Figure 4:
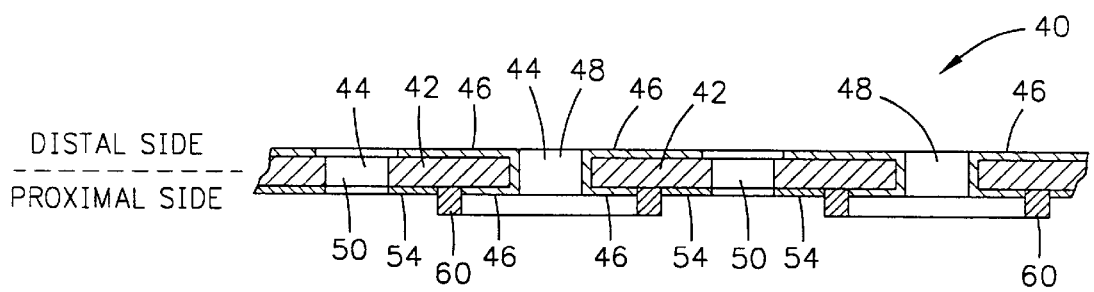
FIG. 4 is an enlarged broken cross-sectional view of an electrode assembly according to the present invention taken through the line 4—4 of FIG. 3.

Turning now to FIG. 4, an enlarged broken cross-sectional view of an electrode assembly 40 according to a preferred embodiment of the present invention taken through the line 4—4 of FIG. 3 is shown. Of particular interest in this view is that one can see that the first electrode 46 extends through the first portion 48 of the plurality of through holes 44 and onto the proximal side. Further, one can see that the insulating barrier 60 extends above the surface of the electrodes and electrically isolates the first electrode 46 from the second electrode 54. The spacing between the first and second electrodes 46, 54 is defined by the insulating barrier 60.

The embodiment of the electrode assembly 40 shown in FIGS. 2, 3, and 4 is purely for illustration purposes. The final configuration will depend on the particular application. As a result, the overall size, shape, and thickness may vary. The size, shape, number, and location of the plurality of through holes 44 may vary. The shape, thickness, and location of the first electrode 46 and the second electrode 54 may vary. The shape, thickness, and location of the insulating barrier 60 may vary. In fact, the insulating barrier 60 may not be necessary at all and may be replaced with an air gap between the first electrode 46 and the second electrode 54.

In the preferred embodiment, the electrode assembly 40 is manufactured using the same techniques used to create printed circuit boards. The carrier 42 is a thin flexible film which allows the electrode assembly 40 to be contoured to the tissue surface which generally has an irregular shape. In one embodiment, the plurality of through holes 44 are provided in part so that drugs and genes can be supplied from a reservoir (not shown) on the distal side and pass through the plurality of through holes 44 to the tissue surface. The insulating barrier 60 is a soldermask which reduces the flow of current directly between the first electrode 46 and the second electrode 54 across the tissue surface. However, the first electrode 46 and the second electrode 54 are closely spaced so as to limit the penetration of the field to a shallow layer of the tissue.

The techniques of electroincorporation may also be used with the herein detailed system and electrodes for the delivery of molecules across tissue surface. This technique is more fully disclosed in U.S. Pat. Nos. 5,462,520 and 5,464,386 which are incorporated herein by reference as through fully set forth.

While the invention has been illustrated and described by means of specific embodiments, it is to be understood that numerous changes and modifications may be made therein without departing from the spirit and scope of the invention as defined in the appended claims.

What is claimed is:

1. An electrode assembly for electroporation of a tissue surface, comprising:

a non-conductive carrier having a proximal surface, a distal surface, and a first plurality and a second plurality of through holes from the proximal surface to the distal surface;

a first electrode disposed on at least a portion of the distal surface and extending through at least one of the first and second plurality of through holes and onto at least a portion of the proximal surface for engaging the tissue surface through which to apply an electric field; and a second electrode disposed on at least a portion of the proximal surface and in closely spaced relation with the first electrode adapted for engaging the tissue surface through which to apply an electric field, wherein the through holes enable the passage of a fluid from the distal surface separately to the surface of the respective electrode on the proximal surface.

2. The electrode assembly according to claim 1 wherein the carrier comprises a thin flexible film.

3. The electrode assembly according to claim 1 further comprising an insulating barrier that is disposed on at least a portion of and projecting outward from the proximal surface of the carrier beyond the electrodes for engaging the tissue surface between the first electrode and the second electrode.

4. The electrode assembly according to claim 3 wherein the insulating barrier is a soldermask.

5. The electrode assembly according to claim 1, wherein said first electrode covers substantially the entire distal surface and forms multiple circular portions on said proximal surface; and said second electrode covers substantially said entire proximal surface except for the circular portions covered by said first electrode.

6. The electrode assembly according to claim 5, wherein said circular portions are disposed in an array of multiple rows.

7. The electrode assembly of claim 6, wherein said circular portions are in offset rows.

8. An apparatus for trans-surface molecular delivery, comprising:

a first electrode assembly, comprising:

a non-conductive carrier having a proximal surface, a distal surface, and a first and a second plurality of through holes from the proximal surface to the distal surface;

a first electrode disposed on at least a portion of the distal surface and extending through at least one of the first and a second plurality of through holes and onto at least a portion of the proximal surface for engaging a tissue surface through which to apply an electric field; and a second electrode disposed on at least a portion of the proximal surface and in closely spaced relation with the first electrode for engaging a tissue surface through which to apply an electric field;

a first power supply connected to the first electrode assembly for applying a pulsed electric field of sufficient amplitude to induce pores in the tissue surface; and means for driving molecules through pores in the tissue surface, wherein the through holes enable the passage of a fluid from the distal surface separately to the surface of the respective electrode on the proximal surface.

9. The electrode assembly according to claim 8, wherein said first electrode covers substantially the entire distal surface and forms multiple circular portions on said proximal surface; and said second electrode covers substantially said entire proximal surface except for the circular portions covered by said first electrode.

10. The electrode assembly according to claim 9, wherein said circular portions are disposed in an array of multiple rows.

11. The electrode assembly of claim 9, wherein said circular portions are in offset rows.

12. An apparatus for trans-surface molecular delivery, comprising:

a first electrode assembly, comprising:

a non-conductive carrier having a proximal surface, a distal surface, and a plurality of through holes from the proximal surface to the distal surface;

a first electrode disposed on at least a portion of the distal surface and extending through at least a portion of the plurality of through holes and onto at least a portion of the proximal surface, and a second electrode disposed on at least a portion of the proximal surface and in closely spaced relation with the first electrode for engaging a tissue surface through which to apply an electric field;

a first power supply connected to the first electrode assembly for applying a pulsed electric field of sufficient amplitude to induce pores in the tissue surface; and means for driving molecules through pores in the tissue surface, wherein said means for driving comprises:

a second electrode assembly spaced from the first electrode assembly and comprising at least one of an anode and a cathode; and a second power supply connected to the first electrode assembly and the second electrode assembly for applying a low voltage continuous electric field of a preselected polarity and sufficient amplitude to induce migration of molecules through pores in the tissue surface.

13. An apparatus for trans-surface molecular delivery, comprising:

a first electrode assembly, comprising:

a non-conductive carrier having a proximal surface, a distal surface, and a plurality of through holes from the proximal surface to the distal surface;

a first electrode disposed on at least a portion of the distal surface and extending through at least a portion of the plurality of through holes and onto at least a portion of the proximal surface, and a second electrode disposed on at least a portion of the proximal surface and in closely spaced relation with the first electrode for engaging a tissue surface through which to apply an electric field;

a first power supply connected to the first electrode assembly for applying a pulsed electric field of sufficient amplitude to induce pores in the tissue surface; and means for driving molecules through pores in the tissue surface, wherein means for driving comprises a pressure source adapted to be in communication with the tissue surface via the plurality of through holes in the carrier of the first electrode assembly for applying pressure of a sufficient amplitude and duration to induce migration of molecules through pores in the tissue surface.

14. An apparatus for trans-surface molecular delivery, comprising:

a first electrode assembly, comprising: a non-conductive carrier having a proximal surface, a distal surface, and a plurality of through holes from the proximal surface to the distal surface;

a first electrode disposed on at least a portion of the distal surface and extending through at least a portion of the plurality of through holes and onto at least a portion of the proximal surface, and a second electrode disposed on at least a portion of the proximal surface and in closely spaced relation with the first electrode for engaging a tissue surface through which to apply an electric field;

a first power supply connected to the first electrode assembly for applying a pulsed electric field of sufficient amplitude to induce pores in the tissue surface; and means for driving molecules through pores in the tissue surface, wherein means for driving comprises an ultrasound source for applying ultrasound of a sufficient amplitude and duration to induce migration of molecules through pores in the tissue surface.

15. An apparatus for trans-surface molecular delivery, comprising:

a first electrode assembly, comprising:
a non-conductive carrier having a proximal surface, a distal surface, and a plurality of through holes from the proximal surface to the distal surface;
a first electrode disposed on at least a portion of the distal surface and extending through at least a portion of the plurality of through holes and onto at least a portion of the proximal surface, and
a second electrode disposed on at least a portion of the proximal surface and in closely spaced relation with the first electrode for engaging a tissue surface through which to apply an electric field;

a first power supply connected to the first electrode assembly for applying a pulsed electric field of sufficient amplitude to induce pores in the tissue surface; and means for driving molecules through pores in the tissue surface, means for driving comprises means for electroincorporation of molecules for applying electroincorporation of a sufficient amplitude and duration to induce migration of particles containing molecules through pores in the tissue surface.

16. A method of trans-surface molecular delivery, comprising:

providing a first electrode assembly, comprising:
a non-conductive carrier having a proximal surface, a distal surface, and a first plurality and a second plurality of through holes from the proximal surface to the distal surface;
a first electrode disposed on at least a portion of the distal surface and extending through at least one of the first and second plurality of through holes and onto at least a portion of the proximal surface; and
a second electrode disposed on at least a portion of the proximal surface and in closely spaced relation with the first electrode;

engaging a tissue surface with the first electrode assembly;

introducing molecules through at least one of the first and second plurality of through holes and onto at least a portion of the proximal surface;

providing a first power supply connected to the first electrode assembly;

applying a pulsed electric field via the first electrode assembly of sufficient amplitude to induce pores in the tissue surface;

providing means for driving molecules through pores in the tissue surface; and applying means for driving to induce migration of molecules through pores in the tissue surface.

17. The method according to claim 16 wherein the step of providing means for driving comprises the steps of:

providing a second electrode assembly spaced from the first electrode assembly and comprising at least one of an anode and a cathode; and providing a second power supply connected to the first electrode assembly and the second electrode assembly, and wherein the step of applying means for driving comprises the step of applying a low voltage continuous electric field of a preselected polarity and sufficient amplitude to induce migration of molecules through pores in the tissue surface.

18. The method according to claim 16 wherein the step of providing means for driving comprises the step of providing a pressure source in communication with the tissue surface via the plurality of through holes in the carrier of the first electrode assembly and wherein the step of applying means for driving comprises the step of applying pressure to the first electrode assembly of a sufficient amplitude and duration to induce migration of molecules through pores in the tissue surface.

19. The method according to claim 16 wherein the step of providing means for driving comprises the step of providing an ultrasound source and wherein the step of applying means for driving comprises the step of applying ultrasound of a sufficient amplitude and duration to induce migration of molecules through pores in the tissue surface.

20. The method according to claim 16 wherein the step of providing means for driving comprises the step of providing means for electroincorporation of molecules and wherein the step of applying means for driving comprises the step of applying means for electroincorporation of a sufficient amplitude and duration to induce migration of particles containing molecules through pores in the tissue surface.

* * * * *

UNITED STATES PATENT AND TRADEMARK OFFICE
CERTIFICATE OF CORRECTION

PATENT NO. : 6,192,270 B1  Page 1 of 1
DATED : February 20, 2001
INVENTOR(S) : Gunter A. Hofmann, Dietmar Rabussay, Arnt Tonnessen & Lei Zhang It is certified that error appears in the above-identified patent and that said Letters Patent is hereby corrected as shown below:

<u>Title page,</u>
Item [75], add -- Lei Zhang, San Diego, CA --

Signed and Sealed this

Thirtieth Day of October, 2001

Attest:

*Nicholas P. Godici*

NICHOLAS P. GODICI
*Attesting Officer*   *Acting Director of the United States Patent and Trademark Office*